United States Patent [19]

Dutcher et al.

[11] 4,266,552

[45] May 12, 1981

[54] LEAD ANCHORING BOBBIN

[75] Inventors: Robert G. Dutcher, Minneapolis; Edward G. O'Neill, St. Paul, both of Minn.

[73] Assignee: Medtronic, Inc., Minneapolis, Minn.

[21] Appl. No.: 93,342

[22] Filed: Nov. 13, 1979

[51] Int. Cl.³ .............................................. A61N 1/00
[52] U.S. Cl. ................................................ 128/419 P
[58] Field of Search ..................................... 128/419 P

[56] References Cited

U.S. PATENT DOCUMENTS

| 3,244,174 | 4/1966 | Wesbey et al. | 128/419 P |
| 3,598,128 | 8/1971 | Chardack | 128/419 P |
| 3,880,169 | 4/1975 | Starr et al. | 128/419 P |
| 3,913,587 | 10/1975 | Newash | 128/419 P |
| 4,094,321 | 6/1978 | Muto | 128/419 P |
| 4,141,752 | 2/1979 | Shipko | 128/419 P |
| 4,144,889 | 3/1979 | Tyers et al. | 128/419 P |

*Primary Examiner*—William E. Kamm
*Attorney, Agent, or Firm*—John L. Rooney; Joseph F. Breimayer; Lew Schwartz

[57] ABSTRACT

The lead anchoring bobbin for containing a transvenous pacing lead at an entry site in human tissue and including a grooved bobbin and buttons which frictionally engage and detain the lead on either side of the bobbin. The lead anchoring bobbin is made of medical silicone rubber or like material.

6 Claims, 5 Drawing Figures

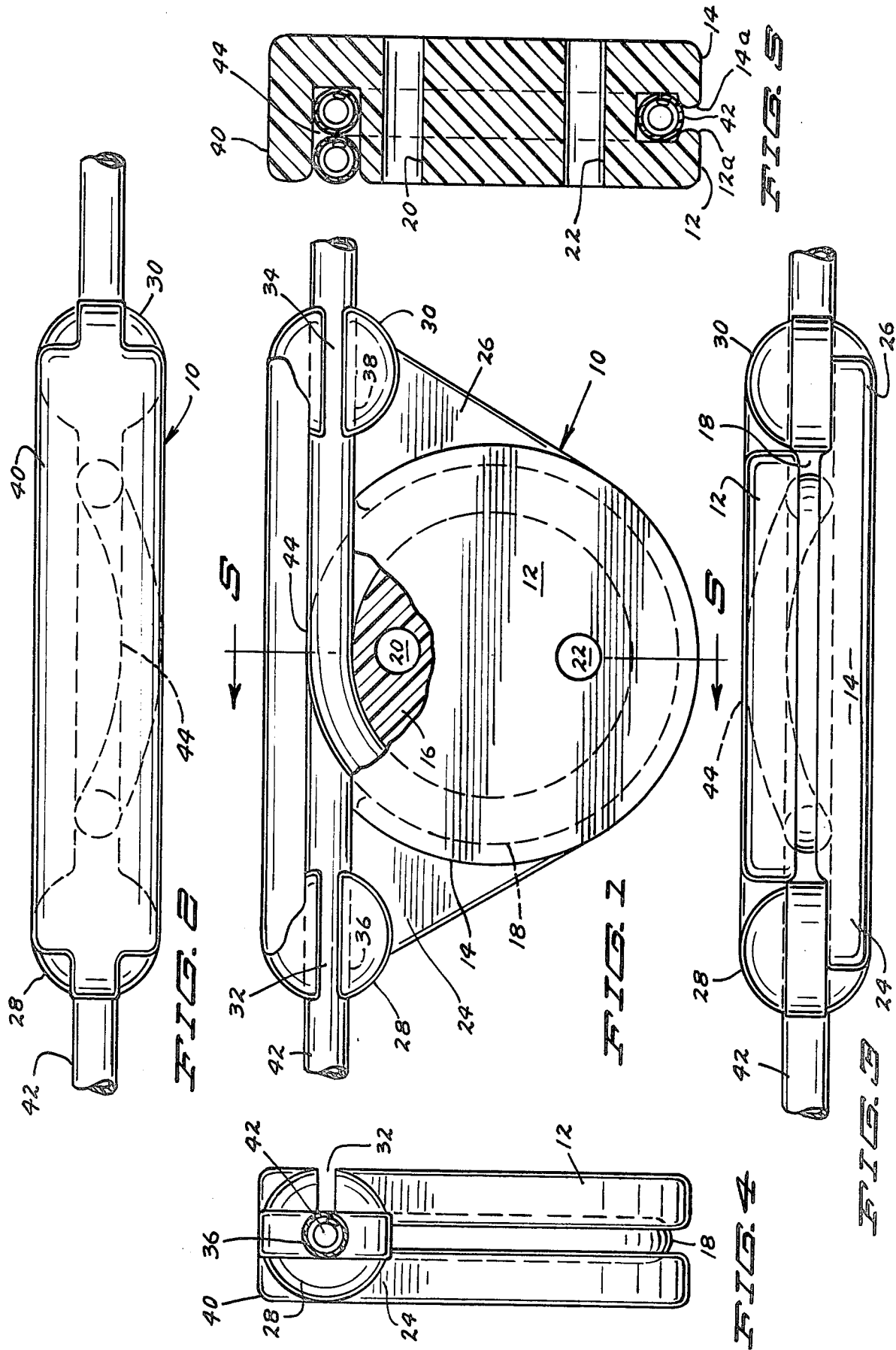

LEAD ANCHORING BOBBIN

BACKGROUND OF THE INVENTION

1. Field of the Invention

The present invention relates generally to a surgical device, and more importantly, pertains to a transvenous pacing lead anchoring bobbin for containing a transvenous pacing lead at an entry site in human tissue.

2. Description of Prior Art

In the past, it has always been a prior art practice to secure transvenous pacing leads by tying the lead off to a vein or using an anchoring sleeve. When the transvenous pacing lead was tied off to a vein, sometimes the lead would work its way free and no longer be secured at the point of tieoff. When the lead was secured to an anchoring sleeve, the lead would also sometimes tend to work loose from the anchoring sleeve. Further, neither tying the pacing lead off at the vein or using an anchoring sleeve provided for strain relief of the transvenous pacing lead at the site of a fixation.

The present invention overcomes the disadvantages of prior art problems by providing a lead anchoring bobbin.

SUMMARY OF THE INVENTION

The present invention provides a lead anchoring bobbin for use with the transvenous pacing lead for containing a transvenous pacing lead at an entry site in human tissue.

According to one embodiment of the present invention, there is provided a lead anchoring bobbin including a bobbin having a groove which accepts a transvenous pacing lead and includes a flat truncated portion extending across the top of the bobbin, wings extending outwardly at an oblique angle from each other and substantially in line and parallel to the top truncated portion of the bobbin, each of the wings including a hole running therethrough and substantially parallel and in line with the truncated top portion and a slit providing for communication of the transvenous pacing lead to said hole, and suture holes provided within the circumference of the groove of the bobbin whereby the transvenous pacing lead is inserted through a slit to engage in a first hole of the first wing, engaged around a groove in the bobbin, overlap the lead, and inserted through the slit to engage in the hole of the second wing thereby providing for a loop tightened on the bobbin at the visible entry site of a vein, strain relief of the transvenous pacing lead at the site of entry into a vein, and providing for anchoring of the transvenous pacing lead to tissue.

One significant aspect and feature of the present invention is that the lead anchoring bobbin provides a visible loop for the transvenous pacing lead which is visible not only to the human eye but also by X-ray.

Another significant aspect and feature of the present invention is that the lead anchoring bobbin prevents easy withdrawal of the transvenous pacing lead in that the lead is firmly affixed to the lead anchoring bobbin and the lead anchoring bobbin is sutured to human tissue.

A further significant aspect and feature of the present invention is that the lead anchoring bobbin acts as strain relief holding the lead and the lead anchoring bobbin, and prohibits the lead from relocating within the human body.

BRIEF DESCRIPTION OF THE DRAWINGS

Other objects and many of the attendant advantages of this invention will be readily appreciated as the same become better understood by reference to the following detailed description when considered in connection with the accompanying drawing in which like reference numerals designate like parts throughout the FIGURES thereof and wherein:

FIG. 1 illustrates a plan view of a lead anchoring bobbin, the present invention, partly in cross-section;

FIG. 2 illustrates a top view of the lead anchoring bobbin;

FIG. 3 illustrates a bottom view of the lead anchoring bobbin;

FIG. 4 illustrates an end view of the lead anchoring bobbin; and

FIG. 5 illustrates a cross-section view taken along line 5—5 of FIG. 1.

DETAILED DESCRIPTION OF THE PREFERRED EMBODIMENT

FIG. 1, which illustrates a plan view of a lead anchoring bobbin 10, the present invention, partly in cross-section, shows a lead anchoring bobbin 10 of medical silicone rubber or like material including a truncated circumferential disc 12 having an outwardly extending circumferential ring 12a as illustrated in FIG. 5 and opposing truncated circumferential disc 14 having an outwardly extending circumferential ring 14a as illustrated in FIG. 5, and a truncated circumferential disc 16 of a diameter less than that of the truncated circumferential discs 12 and 14 thereby forming a groove 18 between the discs 14 and 16. Suture holes 20 and 22 extend entirely through the discs 12–16. Left wing 24 and right wing 26 extend outwardly from the truncated circumferential disc 14 and attached thereto. Left button 28 and right button 30 affix to the left and right wings 24 and 26 respectively. Left button 28 includes a slit 32 extending downwardly to a longitudinal hole 36. Right button 30 includes a slit 34 extending downwardly to a longitudinal hole 38. A longitudinal member 40 connects the top portion of the left button 28 to the top portion of the right button 30 and also connects to the top of the truncated circumferential disc 14. The longitudinal member 40 provides structural strength and alignment for a transvenous pacing lead 42 but is not to be construed as a limiting structural element of the present invention.

Transvenous pacing lead 42 engages through the left slit 32 into the left hole 36 of the left button 28, winds around and engages within the groove 18 between the truncated circumferential discs 12 and 14 and against truncated circumferential disc 16 at point 44 and engages out through the right hole 38 of the right button 30, or vice-versa depending on whether the left side or the right side is closest to the vein entry site.

FIG. 2 illustrates a top view of the lead anchoring bobbin 10. All numerals correspond to those elements previously described.

FIG. 3 illustrates a bottom view of the lead anchoring bobbin 10. Likewise, all numerals correspond to those elements previously described.

FIG. 4 illustrates an end view lead anchoring bobbin 10. Again, all numerals correspond to those previously described.

FIG. 5, which illustrates a cross-sectional view taken along line 5—5 of FIG. 1, shows specifically the outwardly extending circumferential rings 12a of the partially truncated disc 12 and 14a of the partially trunted disc 14. Circumferential rings provide closed area to accommodate the transvenous pacing lead 42.

PREFERRED MODE OF OPERATION

The lead anchoring bobbin 10 can be manufactured from silicone rubber or any like material having capabilities of being sterilized and implanted in the human body.

In use, the transvenous pacing lead 42 is first slid down through the left slit 32 and engaged into the left hole 36 of the left wing 24, wound around and engaged into the groove 18 formed between the outwardly extending circumferential rings 12a and 14a of the truncated circumferential discs 12 and 14 adjacent to and against the smaller truncated circumferential disc 16, overlapping at point 44, down through the right slit 34, and engaged into the right hole 38 on the right wing 26 of the right button 30 or vice-versa. Subsequently, the lead 42 is sutured to the lead anchoring bobbin 10 as the lead anchoring bobbin 10 is sutured to tissue with sutures through suturing holes 20 and 22. The circumferential rings 12a and 14a frictionally retain the lead 42 into the groove between the two discs 12 and 14. The lead 42 can also be wound from right to left.

The lead anchoring bobbin 10 provides for a tightened transvenous pacing lead 42 closed loop which closes on itself at the bobbin site providing visible entry into the vein and strain relief of the transvenous pacing lead 42 in addition to providing anchoring for the transvenous pacing lead 42 to tissue. The closed loop of the lead 42 frictionally retains itself about the bobbin 10. The slotted right and left buttons 28 and 30 in effect form opposing tabs about each side of the lead 42 which provides further strain relief at each of the buttons 28 and 30.

Various modifications can be made to the lead anchoring bobbin 10 of the present invention without departing from the apparent scope thereof.

Having thus described the invention, what is claimed is:

1. Lead anchoring bobbin for use with an implantable lead having proximal and distal ends for attaching to human tissue comprising:
   a. anchoring means having two diametrically opposed partial circumferential discs and a partial truncated disc of a smaller diameter than said two discs, said smaller partial circumferential disc positioned and secured between said two partial circumferential discs, whereby said implantable lead is anchored within a groove formed between said two partial circumferential discs;
   b. at least one retaining means adjacent to said anchoring means for frictionally retaining said implantable lead adjacent to said anchoring means having at least one wing extending outwardly from one of said two partial circumferential discs, said wing including a button having a hole and a slit to said hole whereby said hole retains said lead within said button; and
   c. at least one suturing means for suturing said anchoring means retaining said loop to said human tissue whereby said anchoring means provides for anchoring of said implantable lead to tissue.

2. Lead anchoring bobbin of claim 1 wherein said at least one wing further comprises:
   a left wing and a right wing extending outwardly from one of said two partial circumferential discs, including said hole and said slit to said hole on each of said wings whereby each of said hole and slit form tabs on each side of said button thereby providing strain relief for a lead.

3. Lead anchoring bobbin of claim 2 wherein said slits, holes and buttons are in line.

4. Lead anchoring bobbin of claim 3 comprising a longitudinal member extending outwardly from one of said two partial circumferential discs thereby connecting said retaining buttons.

5. Lead anchoring bobbin for use with an implantable lead having proximal and distal ends and for suturing to human tissue comprising:
   a. anchoring means having a substantially circular circumference for fixedly attaching a loop of said implantable lead by frictionally engaging said loop of said implantable lead intermediate said proximal and distal ends;
   b. at least one retaining means adjacent to said anchoring means for frictionally retaining said implantable lead adjacent to said anchoring means; and
   c. at least one suturing means having at least one suturing hole extending through all of said discs whereby suture attaches said lead anchoring bobbin to human tissue and said lead to said lead anchoring bobbin.

6. In combination, lead anchoring bobbin and transvenous pacing lead for use in human tissue comprising lead anchoring bobbin including a bobbin having a circumferential groove in said bobbin and a flat truncated portion running across the top of said bobbin, outwardly extending wings at an oblique angle from each other extending from one side of said bobbin and substantially parallel with said top truncated portion of said bobbin, each of said wings including a retaining hole running therethrough, substantially parallel and in line with said top truncated portion and a slit through each of said wing to each of said hole, and suture holes within the circumference of said groove of said bobbin and a transvenous pacing lead of longitudinal length whereby said transvenous pacing lead is inserted through said slit into said hole of said wing, wound around said groove in said bobbin, overlapping said lead at said truncated portion and inserted through said slit into said hole of said other wing thereby providing for a tight loop on said bobbin, visible entry site in a vein, and strain relief of said transvenous pacing lead at site of entry into said vein and providing for anchoring of said transvenous pacing lead wound on said lead anchoring bobbin to human tissue, and suturing said lead anchoring bobbin with sutures to said human tissue.

* * * * *